US009615796B2

(12) United States Patent
Coucke

(10) Patent No.: US 9,615,796 B2
(45) Date of Patent: Apr. 11, 2017

(54) PATIENT SUPPORT DEVICE FOR PRONE IMMOBILIZATION

(71) Applicants: Universite de Liege, Angleur (BE); Centre Hospitalier Universitaire de Liege, Liege (BE)

(72) Inventor: Philippe Coucke, Les Waleffes (BE)

(73) Assignees: UNIVERSITE DE LIEGE, Angleur (BE); CENTRE HOSPITALIER UNIVERSITAIRE DE LIEGE, Liege (BE)

( * ) Notice: Subject to any disclaimer, the term of this patent is extended or adjusted under 35 U.S.C. 154(b) by 186 days.

(21) Appl. No.: 14/386,194

(22) PCT Filed: Mar. 15, 2013

(86) PCT No.: PCT/EP2013/055492
§ 371 (c)(1),
(2) Date: Sep. 18, 2014

(87) PCT Pub. No.: WO2013/139713
PCT Pub. Date: Sep. 26, 2013

(65) Prior Publication Data
US 2015/0034091 A1 Feb. 5, 2015

(30) Foreign Application Priority Data

Mar. 19, 2012 (EP) ...................................... 12160081
Oct. 25, 2012 (EP) ...................................... 12189876

(51) Int. Cl.
*A61G 13/12* (2006.01)
*A61B 5/00* (2006.01)
(Continued)

(52) U.S. Cl.
CPC ............ *A61B 5/708* (2013.01); *A61B 6/0421* (2013.01); *A61B 6/0435* (2013.01); *A61N 5/10* (2013.01); *A61N 2005/1097* (2013.01)

(58) Field of Classification Search
CPC .. A61G 13/12; A61G 13/121; A61G 13/1235; A61G 13/1245; A47C 15/008;
(Continued)

(56) References Cited

U.S. PATENT DOCUMENTS 5,208,928 A 5/1993 Kuck et al.
6,698,045 B1 * 3/2004 Coppens ................ A61G 13/12
128/869

(Continued)

FOREIGN PATENT DOCUMENTS

WO 2007/018646 A1 2/2007
WO 2009/033035 A1 3/2009

OTHER PUBLICATIONS

P.A. Coucke et al., "Development of an immobilisation device for treatment of patients after breast conserving surgery for mammary carcinoma", in ESTRO 2010 Conference Poster, Sep. 16, 2010, Barcelona, Spain.

*Primary Examiner* — Ophelia A Hawthorne
(74) *Attorney, Agent, or Firm* — Jacobson Holman, PLLC

(57) ABSTRACT

A patient immobilization device for positioning a patient in the prone position for breast irradiation, includes a cephalic module for supporting the head and upper extremities of the patient, a thoracic module for supporting the patient thorax, and shaped to allow at least one breast to extend below the thoracic module, and a caudal module for supporting the pelvis and lower extremities of the patient, wherein the cephalic module is optionally detachable and securable to the thoracic module; wherein the thoracic module is option- (Continued)

ally detachable and securable to the caudal module and the device can be pivoted in an indexed way around a craniocaudal patient axis F.

21 Claims, 17 Drawing Sheets

(51) Int. Cl.
*A61N 5/10* (2006.01)
*A61B 6/04* (2006.01)

(58) Field of Classification Search
CPC ..... A61F 5/3707; A61B 19/203; A61B 5/708;
A61B 6/0421; A61B 6/0435; A61N 5/10;
A61N 2005/1097
See application file for complete search history.

(56) References Cited

U.S. PATENT DOCUMENTS

2007/0003010 A1* 1/2007 Guertin .................. G21K 1/093
378/63
2007/0033735 A1* 2/2007 Formenti ............. A61B 6/0414
5/600

\* cited by examiner

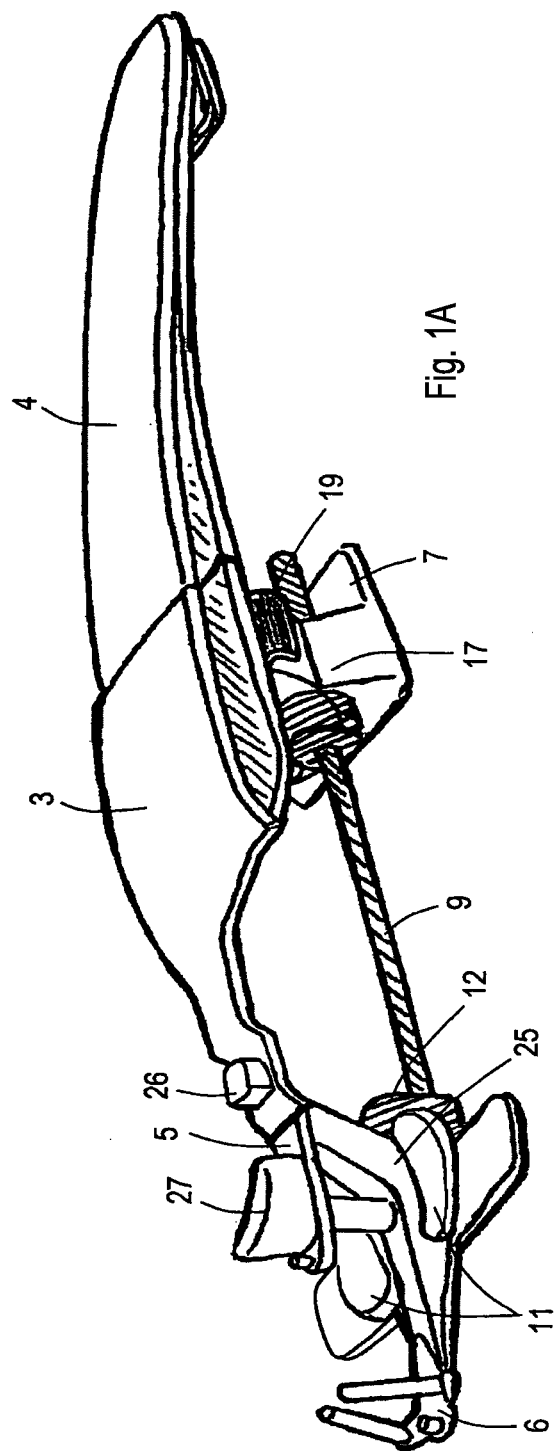

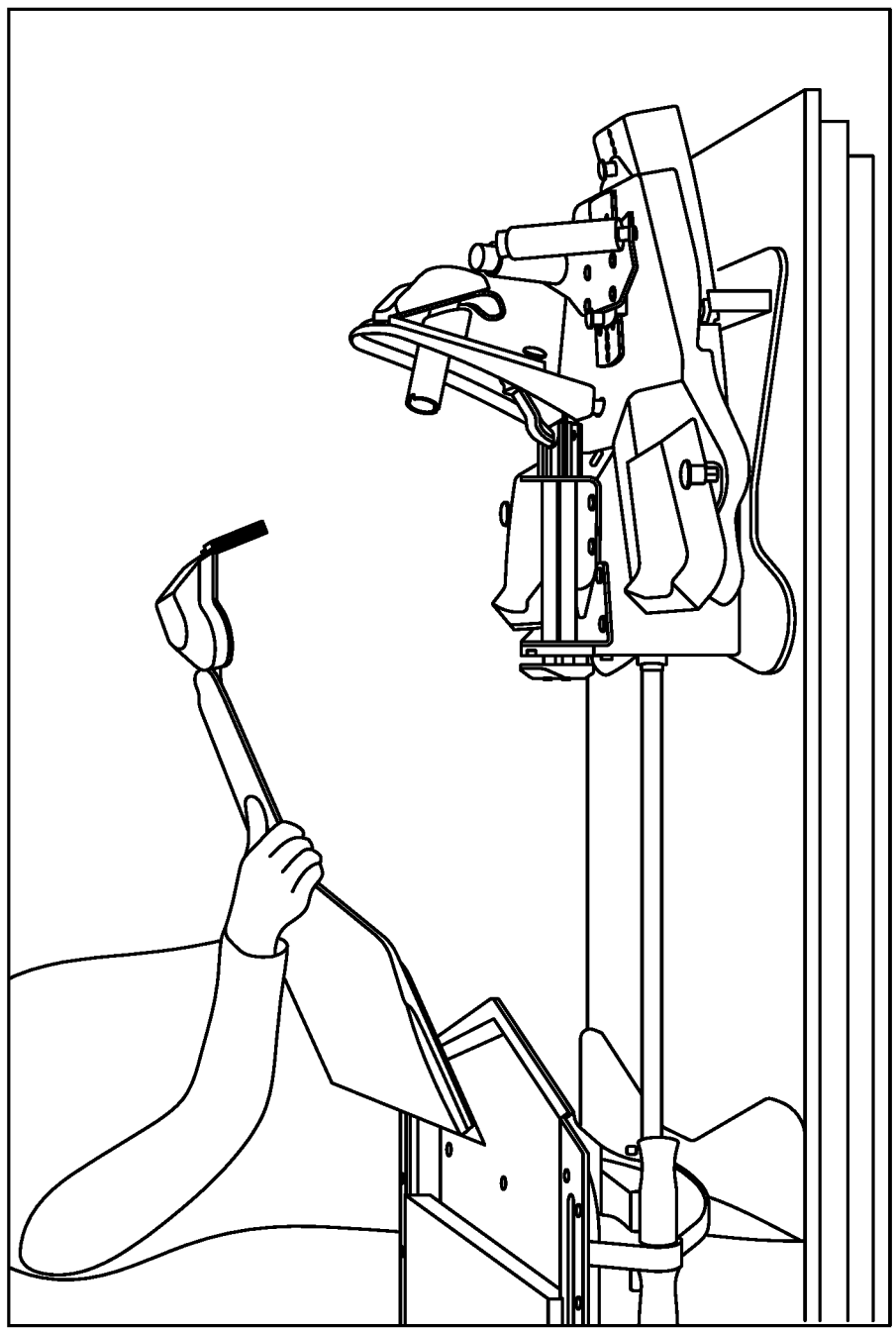

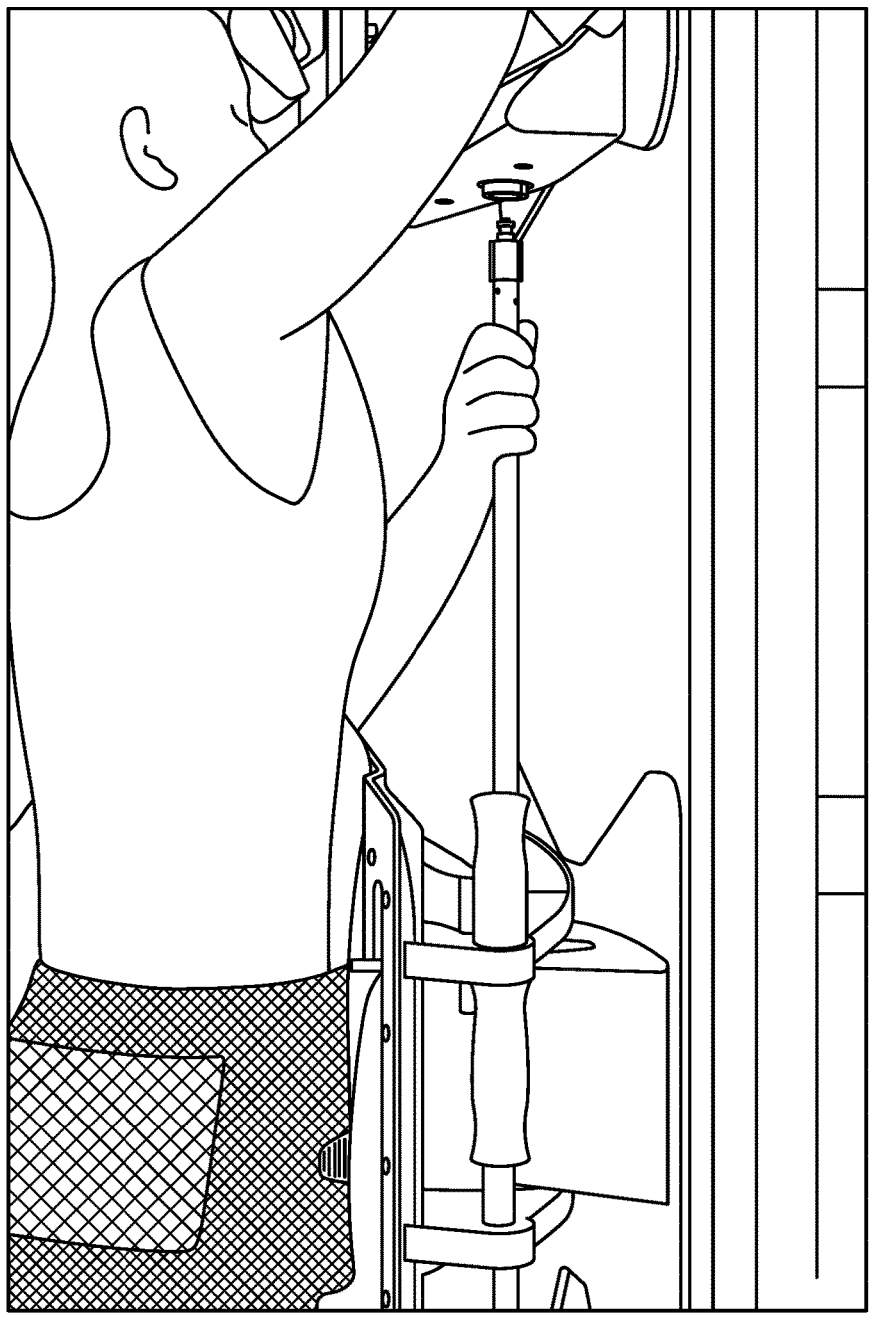

PATIENT SUPPORT DEVICE FOR PRONE IMMOBILIZATION

FIELD OF THE INVENTION

The present invention relates to an adjustable patient immobilization device for repeatably positioning a patient for irradiation treatment of the breast tissue. More specifically, it relates to a patient support and immobilization device for prone positioning for breast irradiation.

BACKGROUND OF THE INVENTION

Radiation therapy plays an important role in the treatment of breast cancer. Devices for positioning patients in a precise and immobilised manner are often used in treating patients using ionizing radiation therapy. In order to control the application of radiation dose to specific localized areas of a patient; it is necessary to precisely position the patient and ensure that patient movement does not occur during the application of the therapy.

Radiation therapy treatment can be applied in either the supine position, i.e. the patient lying down on the back with the face up, as opposed to the prone position, which is face down. The current standard patient position for radiation therapy delivery of breast cancer is the supine position, especially where situation radiation of supraclavicular nodes is intended.

However, potential acute and chronic side effects are related to the treatment in the supine position. The patient may eventually develop acute and chronic pain within the radiation field. The breast itself may develop edema, dermatitis, telangiectasia, ulceration and fibrosis of the skin, with resultant undesirable cosmetic result. Yet further, overexposure of the thorax area may in some cases lead to cardiac and pulmonary complications, including ischemic heart disease, pneumonitis and pulmonary fibrosis.

Recently, prone patient immobilisation devices have been proposed, which typically consist of a board providing a cut out area for the target breast to hang free, sometimes with arm supports, forehead rest and/or lateral wells supporting the lower thorax. However, these presently known patient immobilisation supports have several shortcomings.

The adaptability to individual anatomy is limited, not allowing for adjustment for variations in arm length and/or amplitude of movement, as well as elbow and headrest position.

Yet further, these systems are usually mounted in one piece, creating a frame that is both unwieldy and heavy, and usually therefore only suitable for a single irradiation apparatus.

It therefore is considered highly desirable to have a device and a process that permits a rapid and accurate patient positioning, which offers compatibility with a number of different modern imaging and irradiating devices, and ease to handle by the treating technologists, as well as allowing to optimize planning and dose homogeneity within the target to minimize the side effects of the treatment.

Yet further, it would be highly desirable to enlarge the treatment space corresponding to the region of interest to be treated (thorax/breast) to allow more degrees of freedom for beam angulations, including non-coplanar beam orientations.

The present invention overcomes these shortcomings providing a durable patient support device for immobilizing a patient and allows precise, efficient and repeatable adjustability of the patient prone position.

SUMMARY OF THE INVENTION

Accordingly, the present invention relates to a patient immobilisation device for positioning a patient in the prone position for breast irradiation, comprising a cephalic module for supporting the head and upper extremities of the patient, a thoracic module for supporting the patient thorax, and shaped to allow at least one breast to extend below the thoracic module, and a caudal module for supporting the pelvis and lower extremities of the patient, wherein the cephalic module is optionally detachable and securable to the thoracic module;

wherein the thoracic module is optionally detachable and securable to the caudal module; and wherein the combined device is indexed pivotably around the craniocaudal patient axis F and is adaptable to be reproducibly secured to a treatment table.

The present invention is uniquely adjustable, and it is capable of repeatable positioning a patient by immobilizing the patient's head, shoulders and torso comfortably in the prone position, while giving access to the area that is to be irradiated, while at the same time also minimizing the exposure of tissue to radiation.

The device according to the invention advantageously consists of several different modules that are connected to each other and that are indexed around the cranio-caudal axis F of a person.

A mechanical system at the level of the caudal part and at the level of the cranial part ensures the rotation of the cranio-caudal axis of the device.

The position of the device on a couch top can preferably be changed in connection with a two-pin bar that is compatible with the majority of the treatment tables presently employed.

Advantageously, adapting the device to different person sizes may be made possible by supports in the cranial module under the upper part of the body that may be adjusted to individual needs of a person, and by a support in the caudal module under the lower part of the body.

The shape and the density of the thoracic part of the device is preferably optimized for treatment by clearing to the maximum the area of interest while supporting the thorax part of the patient without deforming this part in such a way that the shape is incompatible with the treatment.

In order to obtain a rotation without deformation, the inventors have now found a way to transfer forces by means of a synchronizing shaft that assures a co-rotation between the mechanical rotation systems of the cranial and caudal part of the device, thereby avoiding the issue with traditional devices where the thoracic module is typically not able to transfer the mechanical rotation force between the cranial and the caudal module.

The synchronizing shaft preferably transfers the rotational forces from the caudal rotating part to the cranial rotating part.

In a particularly preferred embodiment, a rapid connection system may unlock the caudal and cranial rotating parts once they are activated and positioned; once the synchronizing shaft is pulled back, the caudal and cranial rotating parts are locked. The device then advantageously remains locked in its position.

As a safety measure, preferably, an operator cannot engage the rotational movement as long as the synchronizing shaft that assures the co-rotation is not activated.

In a preferred embodiment of the subject device, the rotational movement is engaged by hand at the level of the caudal part.

The rotational movement preferably allows a rotation of a patient around a craniocaudal axis F in angles from −10° to +30°, more preferably of from −8° to +8°, yet more preferably of from −6° to +6°, and most preferably of from −5° to +5°. While the exact indexation is not critical, the rotational movement preferably occurs with increments of 1°.

The modules are optionally secured adaptably and indexed to each other to fit the patient anatomy, and to provide a comfortable position for the patient during treatment. By comfortable position, it is herein understood that a patient can sustain a particular prone position lying on the device essentially without experiencing pain or discomfort as the result of pressure exerted on the contact points of the device for a period of time sufficient to receive a radiation treatment. Moreover the device allows the immobilization of patient of all size in a comfortable and reproducible way.

The device of the present invention is preferably adaptable to most commercially available treatment tables.

The cephalic module preferably comprises i) a base frame structure, ii) a head rest adaptably attached to the base frame, and iii) a pair of handlebars adaptably attached to the base frame, all of which can fully adjustable be mounted onto the base plate. The cephalic module immobilizes the head and arms with the head resting on the head rest, preferably executed as a forehead-chin bracket. The headrest preferably is completely adjustable to compensate for varying head sizes. Without wishing to be bound to any particular theory, it is believed that the adjustment of the headrest, more specifically the forehead support is required in order to decrease discomfort at the pressure point at the sternum.

The cephalic module further preferably comprises means to brace the arms at the elbows. A patient advantageously may gripe the handle bars; which are preferably indexed and fully adjustable to the anatomy of the patient.

The thoracic module portion supports the thorax of the patient, and disengages the breast to be treated from the remainder of the patient body. It comprises a board structure, comprising cut-away section at the breast height. The board structure may be slightly curved, but preferably is essentially flat. The cut-away section becomes a large open space allowing a better treatment of the breast. The open space cut-away section is shaped such as to allow the breast tissue to be treated to hang free through the cut-away section.

The contra lateral side of the patient thorax is supported by the flat or slightly curved board which is preferably padded with suitable padding material such as flexible polyurethane foam to allow a comfortable patient thorax support. The padding is preferably selected such as to minimize pressure on the patient sternum. The curvature of the board is preferably such that it completely supports the patient thorax without need for straps, however, most preferably, the board is flat. This permits the patient to relax, improving reproducibility throughout the simulation and treatment process. The shape and density of the thoracic module, particularly its open space section is optimised for treatment while also supporting the thorax of the patient without deformation of the module during treatment.

In a preferred embodiment according to the invention, a synchronised axis has been used to transfer forces and avoid such deformation of the module during treatment. The synchronised axis improve mechanical resistance of the thoracic module and assures a co-rotation between the thoracic and cephalic module. The synchronised axis is preferably positioned under the module. Such a synchronized axis makes the combined device fully secured, particularly during the patient's craniocaudal rotation.

The caudal module finally passively supports the pelvis and lower extremities of the patient. It preferably provides a gradual slope that stabilizes the patient against rolling from side to side. Additional supports may preferably be present at for the patient knees and ankles to provide further comfort at articulations.

When the different modules are assembled, it is critical for the resulting combined device to have enough mechanical stability and to rotate around the craniocaudal patient's axis in a synchronized way. Such mechanical stability and the synchronised movement are met in the first embodiment with the synchronised axis in its locked position.

When a high energy beam is used for irradiation of the tumour, it is critical that the beam destroys the tumour but not the surrounding healthy tissue. In order to accomplish this objective with acceptable precision, it is critical that the breast tissue is maintained in a precise and fixed position with no possibility of movement. The immobilization of the patient may optionally be improved with a positioning of a mask made of thermoplastic sheets and used, for example, at the lumbar level of the patient.

Reproducible immobilization is essential to a tighter and more conformed treatment field. By precisely positioning and repositioning a patient, a high-energy beam can be repeatably applied to a tumour. This allows for a higher dose of radiation to the gross tumour volume without affecting healthy tissue.

Applicants found surprisingly that this may be achieved by inclining or pivoting the patient according to the bodies' centre axis in order to further enhance the treatment positioning, preferably in a reproducible and accurate positioning.

Accordingly, the device is advantageously indexed pivotably around the craniocaudal patient axis. The craniocaudal patient axis is the central axis running from head to legs. The patient immobilization device of the present invention provides a head, shoulder and torso support and immobilization device that is adaptable to most commercially available treatment tables, is easily adjustable and provides efficient repeatability while allowing to tilt the patient around the craniocaudal axis to a certain degree, to further direct the radiation selectively.

Preferably, the subject device is executed at least in the area of irradiation, i.e. areas that are adjacent to the radiation source in a radiolucent material. Radiolucency is highly desirable, since in radiation therapy, metallic parts may case elastic and inelastic radiation scattering as well as fluorescence which can expose the patient to unnecessary radiation.

While the use of metals can cause unwanted radiation exposure, it may also reduce the desired radiation dose that reaches the target area due to their high radiation absorption compared to polymer and carbon fibre composites preferentially employed in the device according to the present invention.

Accordingly, the device is preferably executed at least in part in a polymeric composite material such as carbon fibre composite material with thermosetting resins, such as epoxy resins and/or polyesters resins. More preferably, the modules of the subject immobilization device may be essentially entirely constructed of non-metallic components to provide radiolucency.

BRIEF DESCRIPTION OF THE DRAWINGS

It is understood that the dimensions may vary from that shown in the drawings and the drawings are presented for illustrative purposes only. The precise shapes and dimensions of the invention can be changed without departing from the object of the present invention. Furthermore, the arrangement and specific design may change without departing from the scope of the invention.

Table 1 shows the terms and relevant reference numbers employed in FIGS. 1 to 3 and 6 to 9; Table 2 shows the possible inclination axis; Table 3 shows the terms and relevant reference numbers employed in FIGS. 4a, 4b, 5, and 10 to 12.

FIGS. 1 to 12 are illustrations of one or more preferred embodiments of the present invention. FIG. 1a shows a three-dimensional depiction of the device. FIGS. 2 to 3 are three-dimensional depictions of preferred embodiments of the modules and/or devices. FIG. 2d illustrates the connection of the caudal module to the cephalic module with the synchronization axis. FIGS. 4a and b show a self-locking mechanism for the rotational movement. FIG. 5 discloses a three-dimensional view of a preferred thoracic module, showing a preferred embodiment of the rotation system. FIGS. 6 to 9 are cross-sectional depictions of a preferred synchronised pivoting system. FIG. 10 discloses a three-dimensional view of a preferred caudal module, showing a preferred embodiment of the rotation system. FIG. 11a shows the self-locked position, and FIG. 11b the locked and co-corotational position. FIG. 12 is a three-dimensional depictation of a preferred device comprising a cephalic, and a combined thoracic and a caudal module, whereby the modules are connected by the corotation synchronisation axis.

TABLE 1

List of terms and reference numbers

Figure 1B:
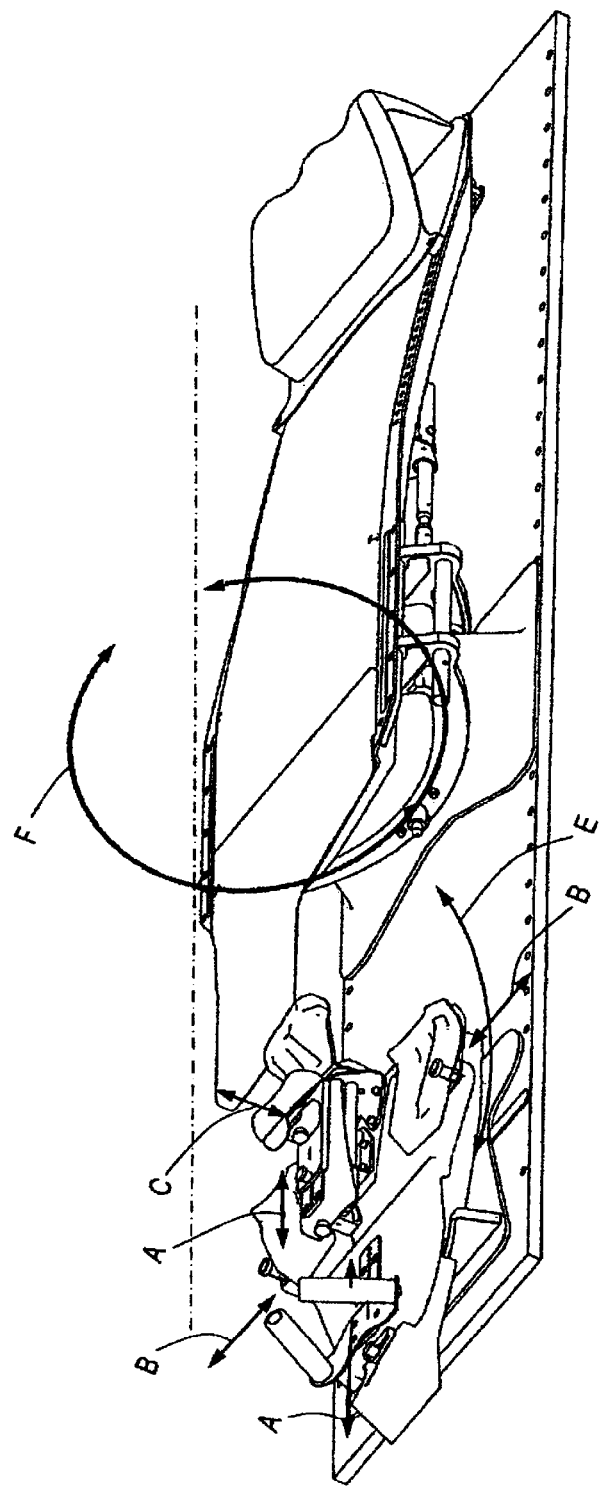
FIG. 1b shows the same device with moving axes for an ergonomic position of the patient.

| Reference Number | Term |
|---|---|
| 1 | Device |
| 2 | cephalic module |
| 3 | thoracic module |
| 4 | caudal module |
| 5 | head rest |
| 6 | Hand rest |
| 7 | base |
| 8 | primary pivoting drive/lock |
| 9 | synchronisation axis/shaft |
| 10 | secondary pivoting drive/lock |
| 11 | elbow rest |
| 12 | Quick disconnect system |
| 13 | alignment bar |
| 14 | Gear |
| 15 | toothed lever |
| 16 | treatment table |
| 17 | curved rack |
| 18 | hinged lever |
| 19 | spring loaded operator grip |
| 20 | Cam |
| 21 | Slit |
| 22 | locking element |

TABLE 1-continued

List of terms and reference numbers

| Reference Number | Term |
|---|---|
| 23 | locking element |
| 24 | locking element |
| 25 | Base Plate |
| 26 | Chin support |
| 27 | Forehead support |

TABLE 2 list of moving axes for comfortable position of the patient
Moving axes for ergonomic assemblies

| Ergonomic assembly | Device | Axe of moving the device | Axe of Interconnection |
|---|---|---|---|
| All the modules | All | F | F |
| Arms support | Hands support | A | E |
|  | Elbow support | B |  |
|  | Arms support | E |  |
| Head support | Chin | Fixed | A |
|  | Forehead | A/C |  |

TABLE 3

| Reference Number | Term |
|---|---|
| 1 | Device |
| 2 | Cephalic module |
| 3 | Thoracic module |
| 4 | Caudal module |
| 5 | Cephalic inclinable support |
| 6 | Cephalic mechanism support |
| 7 | Caudal mechanism support |
| 8 | Caudal inclinable support |
| 9 | Operator grip |
| 10 | Co-rotation shaft |
| 11 | Thoracic module locking |
| 12 | Thoracic module locking arm |
| 13 | Arm indexable supports |
| 14 | Hands indexable supports |
| 15 | Elbows indexable supports |
| 16 | Fronthead indexable support |
| 17 | Chin support |
| 18 | Ankles indexable support |
| 19 | Treatment table |
| 20 | Incline system Trigger |
| 21 | Back thoothed pinion lock lever |
| 22 | Back Thoothed pinion lock |
| 23 | Back curved rack |
| 24 | Incline supports wheels |
| 25 | Quick disconnect mechanism |
| 26 | Front thoothed pinion locking |
| 27 | Front curved rack |
| 28 | Front wheels support |
| 29 | Front thoothed pinion lock lever |
| 30 | Quick disconnect Sliding locking piston |
| 31 | Quick disconnect Sliding locking piston tip |
| 32 | Compressive spring |
| 33 | Balls locking piston |
| 34 | Locking balls |
| 35 | Pinion tube |
| 36 | Co-rotation shaft keys |
| 37 | Stop circlip |
| 38 | Pinion tube slots for corotation |

DETAILED DESCRIPTION OF THE INVENTION

The device according to the invention is preferably adaptable to be reproducibly secured to a treatment table.

In FIG. 1, the patient immobilisation device preferably comprises different interconnected modules arranged to rotate around a longitudinal axe or the craniocaudal patient axis F. The device is also arranged to provide a comfortable and an ergonomic position for the patient during treatment. Preferably, the modules are secured adaptably and indexed to each other to fit the patient anatomy.

The device is advantageously indexed pivotably around the craniocaudal patient axis F. The device preferably further comprises a co-rotation system for controlling of the pivoting motion of at least the cephalic and thoracic module. The patient, once placed on the device, can advantageously be inclined in an angle by means of a subsystem that acts on the whole of the patient immobilisation device. Applicants found that this leads to further distancing of the treated breast from the rest of the body, which was in particular found useful for patients with pendulous breasts.

In order to clear the treatment area as much as possible, the element bridging this area preferably has a reduced, cut-out section. As a consequence this element and its mechanical interface to the adjacent structure may be deformed under load during the inclination movement.

Therefore, to ensure proper alignment, the device advantageously comprises a synchronization system that controls the inclination of the patient immobilisation device when it is moved, as well as keeping the whole system stable and well aligned in static position. The synchronization axis also allows to link the cephalic and the caudal module in a proper aligned way. This concept is referred herein to as the "co-rotation system", and preferably comprises a number of elements. The co-rotation system preferably comprises a) at least a primary lock and at least a secondary lock, and b) at least a synchronizing element that controls and coordinates the movement of the primary and the secondary lock. The primary lock preferably has a human interface allowing an operator to change the inclination of the patient manually. The secondary lock is preferably moved by the movement of the primary lock through the synchronizing element, advantageously in the form of a synchronising axis.

The craniocaudal patient axis F may advantageously run through the patient directly, or preferably may be off-set to a parallel position below the patient. The latter preferably permits to place the pivoting mechanism below the patient and to be disconnected and removed at rest in a position that conveniently does not interfere with the radiation or scanning equipment. In either case, the device permits to place the patient at a position at an angle with respect to the prone position around the actual craniocaudal patient axis F.

The device further preferably comprises a mechanical support structure guiding the pivoting movement of at least the cephalic and thoracic module.

Locking systems referred to as "primary and secondary locks" herein, as well as one or more elements referred to as the "synchronizing axis" that inter-connect the different lock systems and mechanically support structures that guide the inclination movement of the immobilisation device. While the primary lock preferably may have a human interface allowing an operator to change the inclination of the patient manually, the secondary locks preferably cannot be controlled directly by the operator. The locking system preferably holds the neutral (0°) and inclined positions in a safe and mechanically secured way. In the treatment area, the synchronizing axis may be removed to enhance imaging/treatment performance. When the synchronizing axis has been removed the locks are engaged and cannot be released hence in order to move the system the synchronizing axis must be in place.

The device preferably has a capacity to angle the entire board from −10° to +10°, more preferably from 0 to −6°. The pivoting action is preferably indexed in increments of 1°. The angling or pivoting system will preferably be completely incorporated in the system to avoid unnecessary supplementary mechanical tools and reduce the weight.

To optimise the patient positioning in an ergonomic and repetitive way, the device further comprise a head rest (5), a hand rest (6), an elbow rest (11) supports that are arranged to move independently from each other along their respective axe (A to E). As illustrated in FIG. 1b, the hand rest support (6) is arranged to move along axe A; the elbow rest support (11), along axe (B). Both are connected on a base plate also called arm support (25) which move along axe E.

The headrest support comprises an ergonomic forehead support (27) and an ergonomic chin support (26). The chin support and the forehead support are arranged to move each independently along axes A and C and to rotate around axe D.

In a preferred embodiment, the hand rest support (6) and elbow rest support (11) are sliding supports attached on a sliding arm support and the arm support (25) can move along axe E.

Figure 2A:
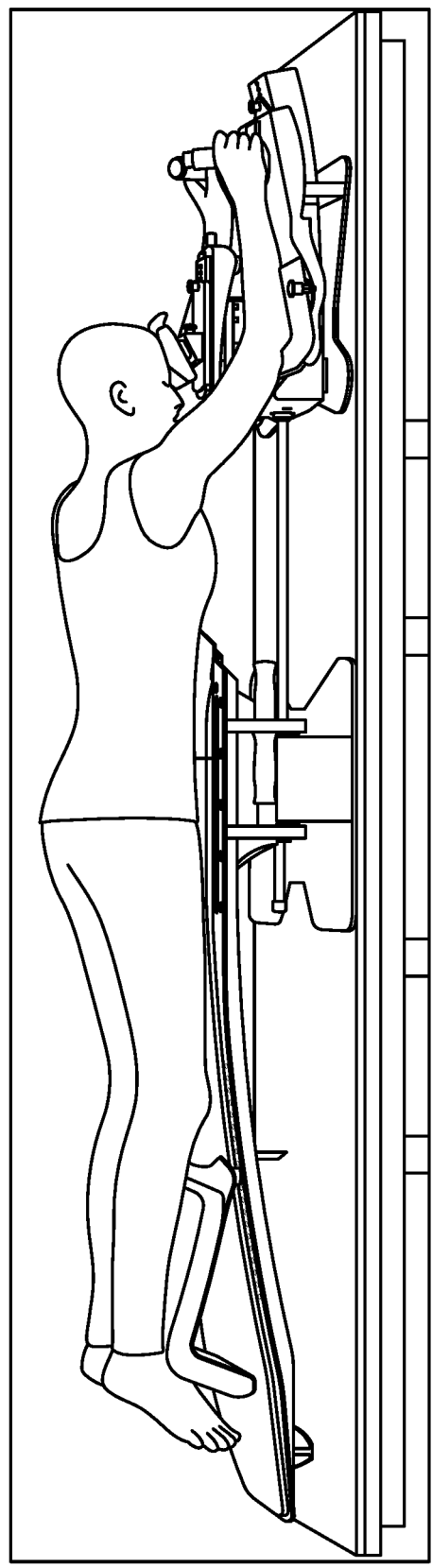
FIG. 2a illustrates an example of immobilization device according to the invention.
Figure 2B:
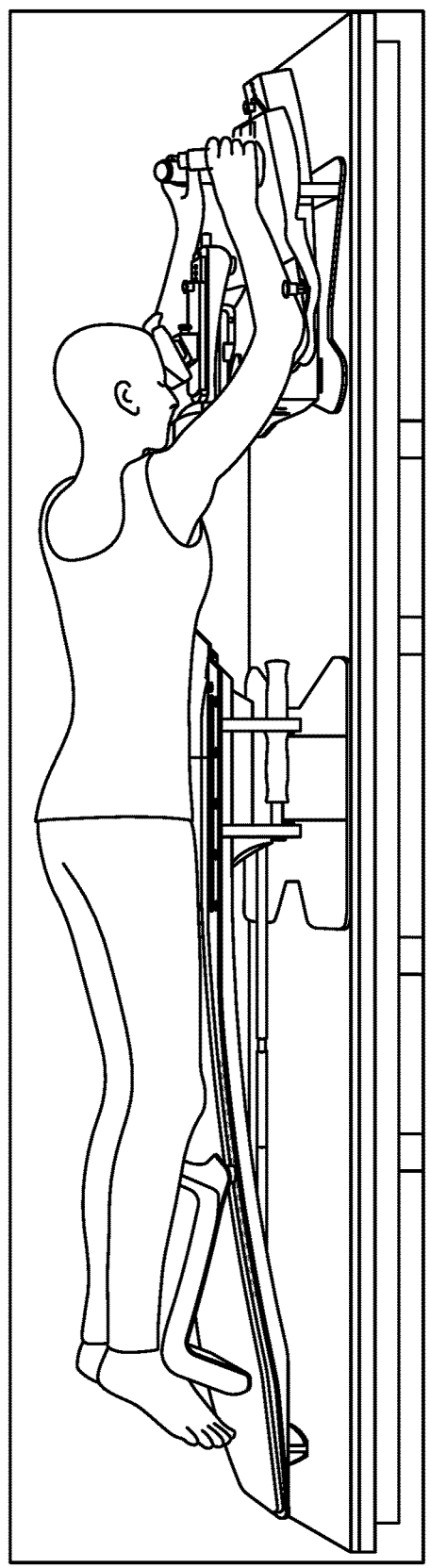
FIG. 2b illustrates a rotation of the immobilization device according to the invention. FOG. 2c illustrates the interconnection of the thoracic module with the cephalic module and the caudal module.

FIG. 2a and FIG. 2b represent an example of embodiment according to the invention wherein the immobilisation device comprises three interconnected modules.

Both cephalic and caudal modules are interconnected through the synchronization axis and the thoracic module in FIG. 2a. In such locked configuration, a rotation of the patient may be engaged to further enhance the treatment positioning. The synchronization axis may further be disconnected as represented in FIG. 2b to allow breast treatment.

FIG. 2c shows an assembly of the immobilization device, particularly how the thoracic module is interconnected with the cephalic module and the caudal module.

FIG. 2d shows the connection of the caudal module to the cephalic module with a synchronization axis. The synchronization axis transfers the rotational forces from the caudal rotating module to the cephalic rotating module. The synchronisation axis can be easily disconnected thanks to a rapid connection system.

The synchronizing axis can then be pulled back but all cephalic, thoracic and caudal modules remain locked. The combined immobilization device remains locked in such position. No rotation is possible at this stage. As a safety measure, an operator cannot engage a rotational movement to the device as long as the synchronization axis that generates rotation, is not engaged.

Figure 3:
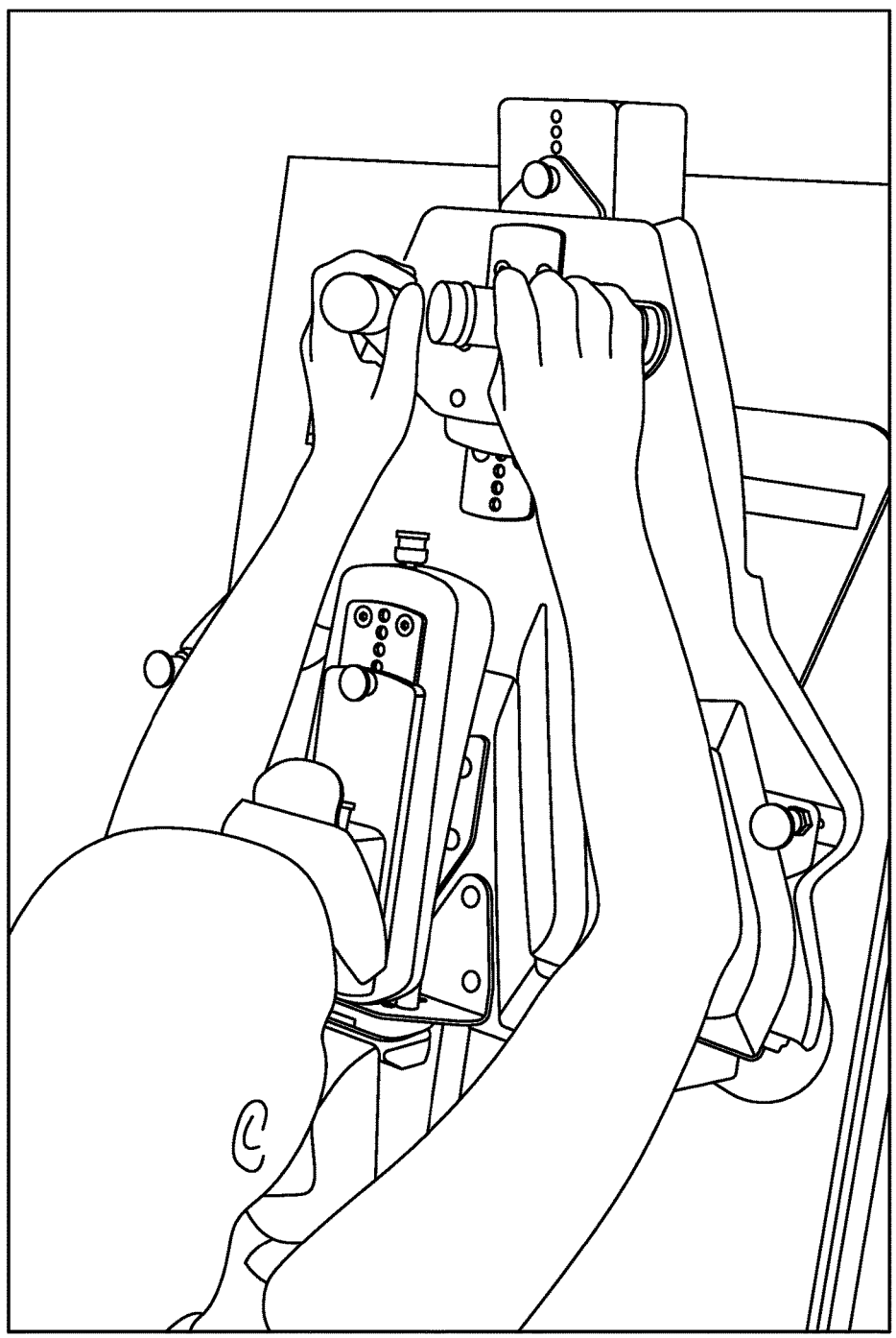

FIG. 3 shows an example of cephalic module including head rest support, hand rest support, elbows rest support positioned on a sliding arm support.

Figure 4:
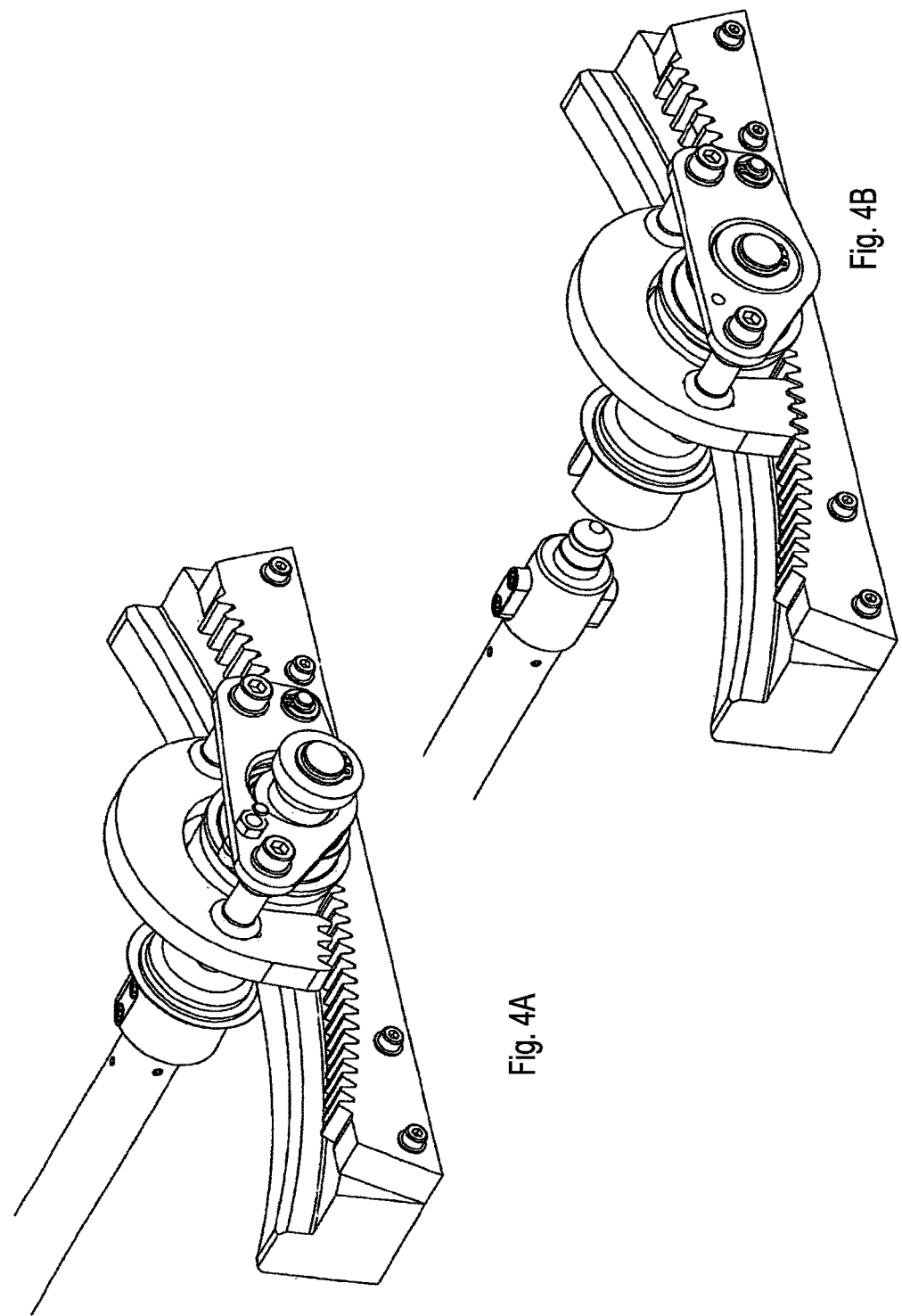

FIGS. 4a and b show a particularly preferred embodiment, of a self-locking rotation lock. FIG. 4a shows the unlocked position upon insertion of the synchronisation axis, and FIG. 4b shows the locked position, upon removal of the synchronisation axis.

Figure 5:
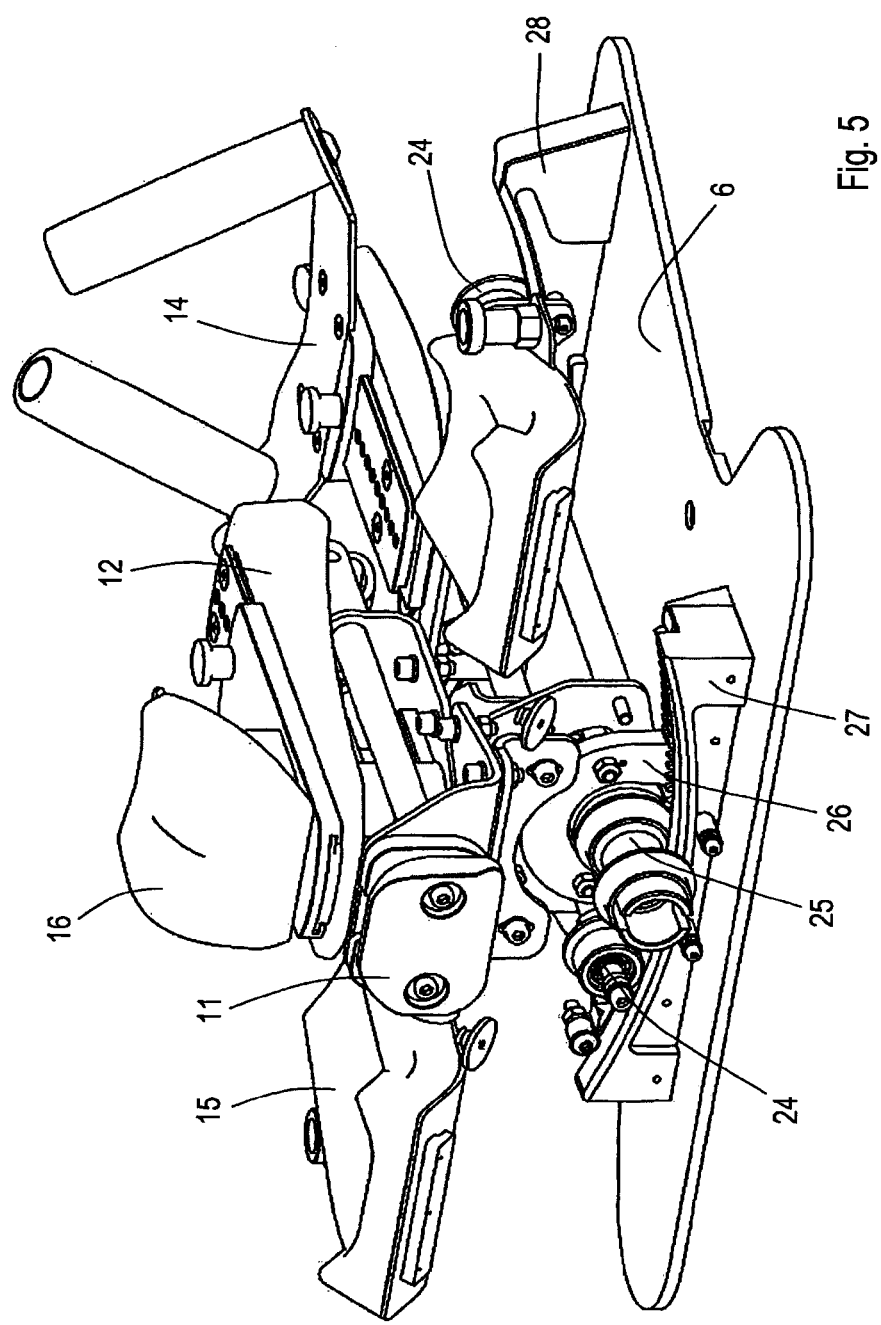

FIG. 5 discloses a three-dimensional view of a preferred thoracic module, showing a preferred embodiment of the rotation system.

Two alignment bars (13) are present (at the cephalic and thoracic portion levels) to ensure identical positioning from day to day.

Figure 6:
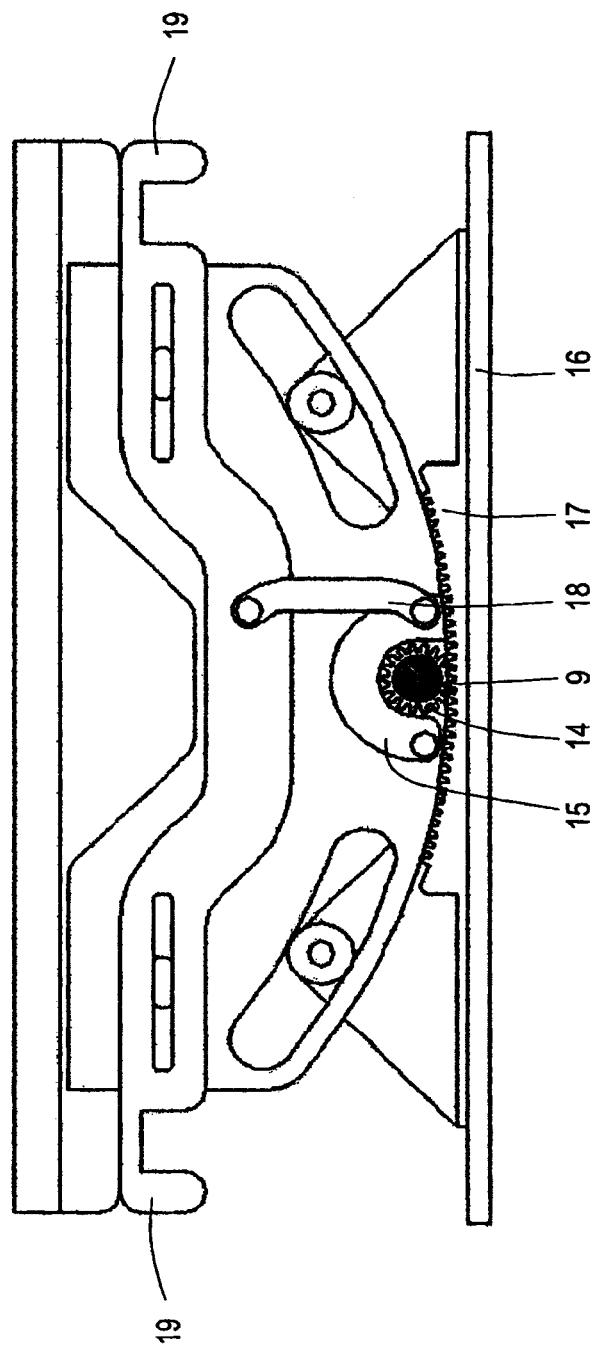

FIG. 6 depicts a preferred embodiment of the device of the present invention for use with a patient in the prone position, specifically the primary lock/drive of the synchronised pivoting element. Herein, the synchronization axis (9)

transfers a rotation between different supporting modules of the patient immobilisation device. The synchronization axis (9) can slide along its centre axis and has coinciding engaging positions with both primary (8) and secondary locks (10). To release the primary lock the operator moves the grip (19). When holding the grip the operator can change the inclination angle of the patient immobilisation device two-ways (CW or CCW) by pushing/pulling. The curved rack (17) is attached to the treatment table (16).

Figure 7:
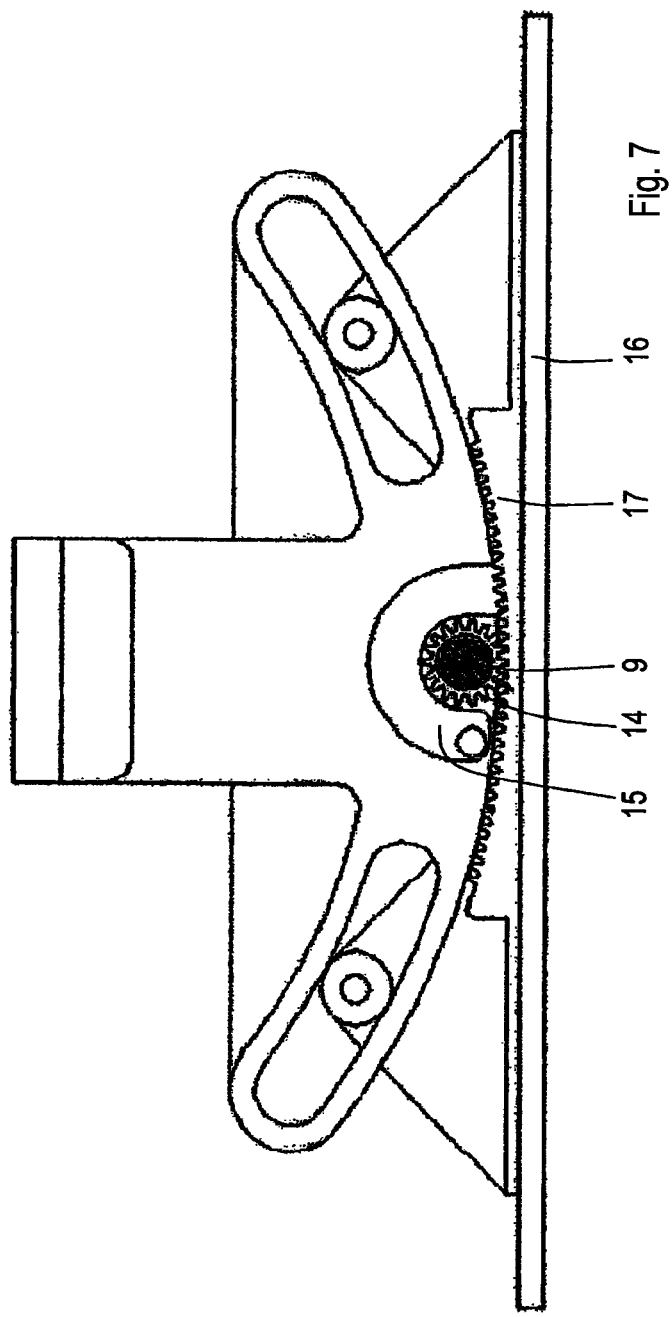

FIG. 7 depicts a preferred embodiment of the device of the present invention for use with a patient in the prone position, namely the side-on view of the secondary lock/drive linked to the first drive by synchronization axis (9). Herein, a toothed lever (15) and a curved rack (17) are linked to synchronization axis (9). The curved rack (17) is attached to the treatment, table (16).

Figure 8:
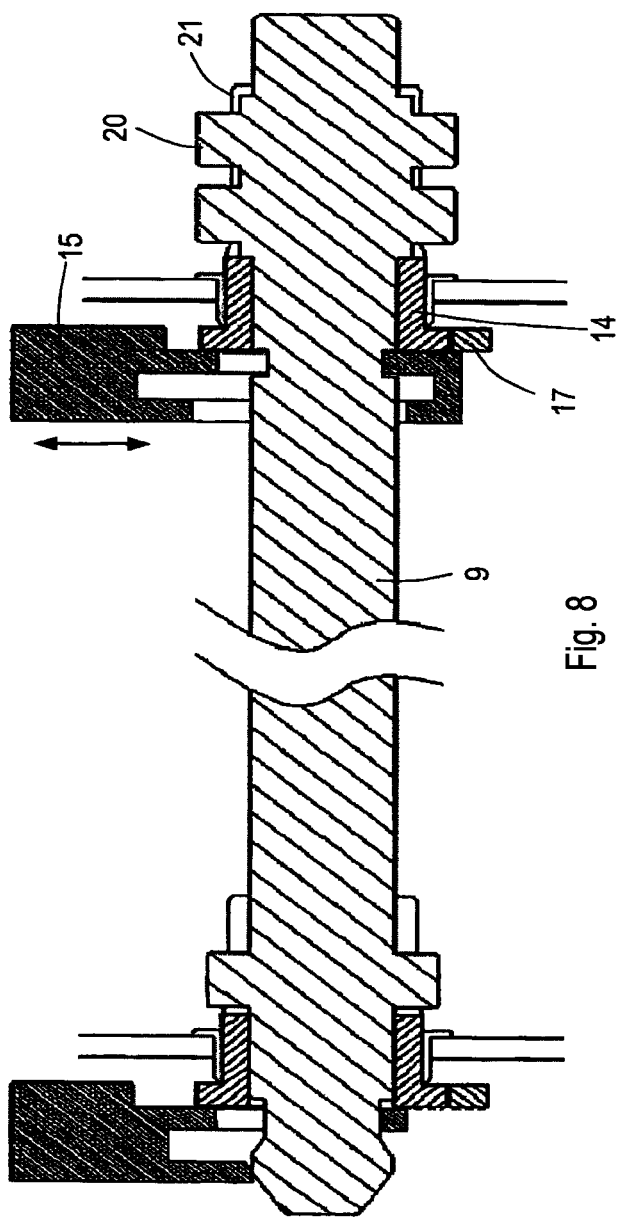

FIG. 8 shows a cross-sectional view of an embodiment of the interconnection between the primary lock. Herein, if the synchronizing axis (9) is not engaged, the tube section of the synchronizing axis blocks the toothed lever (15) down which locking the co-rotation mechanism.

When the synchronizing axis (9) is engaged as described here on FIG. 8, there is a recess in the shaft section tube located at the toothed pinion lever (15) that allows the lever (15) to be activated upward by the spring loaded operator grip (19).
As far the co-rotation shaft (9) is not properly engaged, the operator cannot unlock the co-rotation system. The co-rotation motion is done by the keys (cams) (20) fixed on the synchronizing axis (9) going into the slits of the pinion tube (21).

In an embodiment, the operator activates a spring-loaded grip (19) that moves a hinged lever (18) that then lifts a toothed lever (15) which hereby is disengaged from a curved rack (17). The curved rack is part of the structural support of the patient immobilisation device and is located on a patient positioning table top (16) or similar equipment. A gear (14) transmits the rotation generated by the displacement to the synchronizing axis (9). As follows: as long as the operator holds the grip the inclination position can be changed. Once released hinged lever (18) forces toothed lever (15) back into its locking position onto the curved rack (17). The racks tooth geometry corresponds to a defined step in the inclination, for example 1 degree per tooth position. With the lock freed, i.e. operator holding grip (19), the synchronization axis (9) cannot be removed because a locking element (22) inserted into a slot (23) of the synchronization axis prevents the axis's sliding movement. Consequently when the lock is engaged, i.e grip (19) released, the geometry of the locking element (22) clears the slot of the synchronization axis allowing the operator to slide the axis and at the same time it prevents to disengage the lock. The synchronization axis, when in retracted position, remains in the primary lock, the geometry (diameter) preventing the lock to disengage by blocking element locking element (22).

Figure 9:
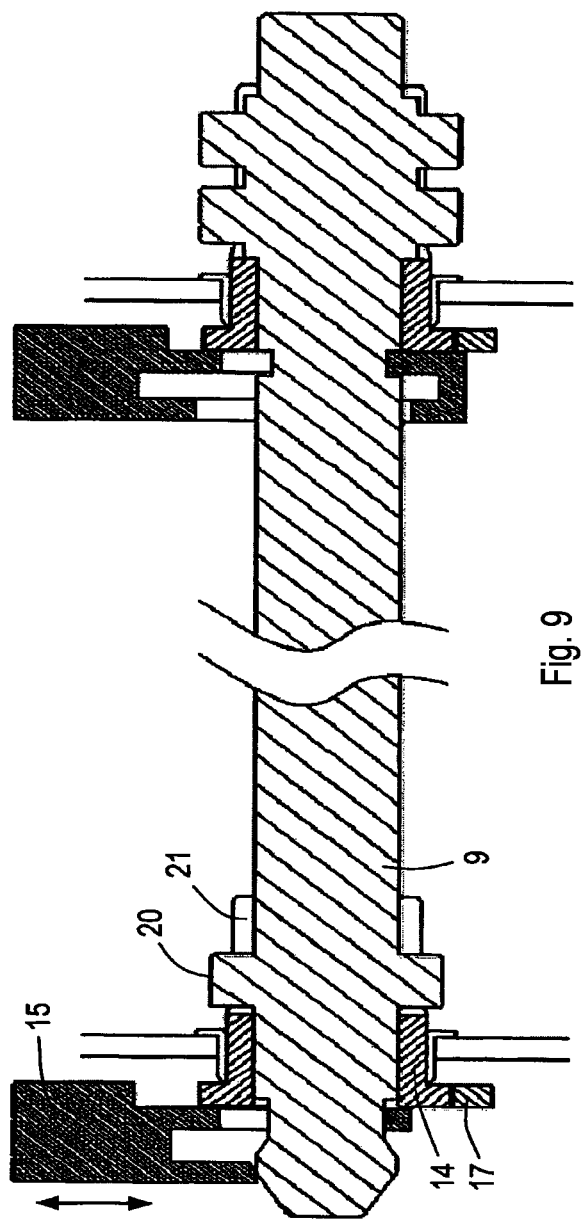

FIG. 9 depicts how the secondary lock not having the human interface is controlled by means of the synchronization axis (9) position within the lock.
As far the shaft is not engaged, the toothed lever (15) is pushing down by a spring and the co-rotation mechanism is locked.
When the shaft (9) is engaged, the shape of the shaft tip pushes the toothed lever up witch unlock the co-rotation mechanism in coordination with the primary lock.
The co-rotation motion is done by the keys (cams) (20) fixed on the shaft (9) going into the slits of the pinion tube (21).

In an embodiment, FIG. 9 depicts how the secondary lock not having the human interface is controlled by means of the synchronization axis (9) position within the lock. With the axis inserted, a gear (14) and curved rack (17) can freely move and thus the inclination position can be modified by the manipulation of the operator of the primary lock, wherein rotational movement is transmitted by means of synchronization axis (9). The synchronization axis interfaces with an element (23) that is directly mounted to toothed fever (15). This element itself has a part (24) hard-mounted on it, the synchronization axis (9) geometry positioning the toothed lever, thereby clearing it from the curved rack (17). When the operator slides the synchronization axis out of the lock, the axis's geometry will move element (14) to engage the toothed lever (15) into the curved rack (17), thus blocking its position. The movement is controlled both ways by the element's (14) two-sided geometry forcing the engagement of both gear and rack. Conversely when the operator slides back the synchronization axis into the lock the gear is released. Part (24) is moves the toothed lever (15) via element (14) and the lock remains released as long as the synchronization axis (9) is in place.

The synchronization axis preferably has a number of cams (20) on along its periphery. Each set of cams is positioned on the axis corresponding to the locations of the different primary and secondary locks. The cam sets are aligned ensuring that ail locks are engaged at the same time and at the same angle. When the operator moves the synchronization axis in its stored position both primary and secondary locks are disengaged in parallel and as a result all the patient immobilisation device's modules are blocked into the same inclined position. When the operator re-inserts the synchronization axis and the cams interface in slots (21) on the different gears, also these slots remain aligned geometrical disposition as described above ensures there is no geometrical conflict.

Figure 10:
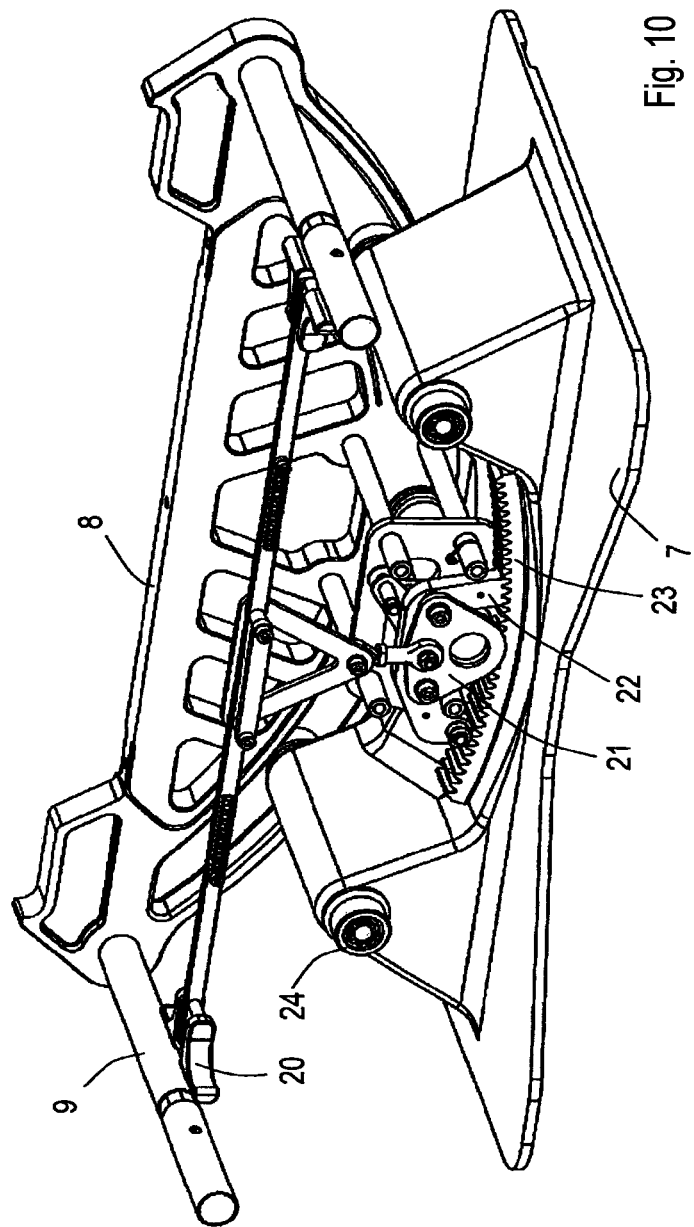

FIG. 10 depicts a further preferred embodiment of the rotation system on the caudal module.

As far the co-rotation shaft (10) is not engaged in corotation position, the shaft section tube blocks the toothed pinion lever (21) down which locks the co-rotation system. When the co-rotation shaft (10) is engaged, there is a recess in the shaft section tube located at the toothed pinion lever (21) that allows the lever (21) to be activated up by the triggers (20). When activated up, the toothed pinion lever (21) release the toothed pinion lock (22) and the operator can incline the system using the hand grips (9).

The co-rotation motion is done by the keys (cams) (36) fixed on the shaft (10) going into the slots of the pinion tube (35). As soon the operator release the trigger (20), the toothed pinion lever is automatically locked down blocking the inclination position and the co-rotation mechanism.
When disengaging the co-rotation shaft (10) from the mechanism, the section of the shaft tube automatically blocks the toothed pinion lever down, which deactivates the triggers (20) automatically. An operator can now no longer incline the table. Inclination position and co-rotation mechanism are locked.

In a preferred embodiment, as depicted in FIG. 11, the corotation shaft (10) is operably locked by a removable quick-release a ball mechanism which allows the following operations: When in corotation mode, the shaft is locked along its axis so that it cannot be removed, but is held firmly in place by a set of balls (37) moving in a sliding sleeve (29). The sliding sleeve is in forward position, so that in this position, the pinion lock is open. The corotation shaft moves the pinion (30) through keys installed on the shaft.

To release the corotation shaft (9), backward motion of the corotation shaft moves back the sliding sleeve (29), which locks the pinion (30) through pinion lock cam (30) moving the pinion lock (28).

If the pinion lock (28) cannot be locked, for example between two indexed angular positions in the rack (17), the sliding sleeve (29) cannot, be moved back and the corotation shaft is not released until an indexed position is achieved.

When an indexed position is achieved, the sliding sleeve (29) can be moved backward. The locking balls (37) reach a wider diameter in the stepped hole (33), thereby releasing the corotation shaft (9).

During the release of the corotation shaft (9), the ball spigot (32) locks the balls (37) in their position, thus preventing any movement of the sliding sleeve (29) and consequently securing the pinion lock 28).

As far the co-rotation shaft is not engaged, the co-rotation is not possible. Co-rotation system lock release: There are reservations in the sliding locking piston (30) containing the locking balls (34). When the corotation shaft is removed, the sliding locking piston (30) is in the rear position. It cannot go further back because of the Stop circlip (37); and it cannot go forward because the Balls locking piston (33) maintains the locking balls (34) in the reservation of the Pinion tube (35).

In this position, the sliding locking piston tip (31) maintains the front toothed pinion lock lever (29) down. This lever (29) controls the front toothed pinion locking (26) and so, the system is locked.

When engaging the corotation shaft (10) into the sliding locking piston (30), the head of the shaft compress the spring (32) and push the balls locking piston (33) that unlock the balls.

The balls are going into the grove of the shaft head and so the sliding locking piston (30) can slide forward, pushed by the corotation shaft head through the balls.

In forward position, the shape of the sliding piston tip (31) allows to make the front toothed pinion lock lever free. This lever is pulled up by a spring and activate the front toothed pinion lock (26) to the up which unlock the mechanism.

The co-rotation motion is done by the Corotation keys (36) going into the slots of the Pinion tube (38)

Co-rotation system locking: When removed, the shaft pulls the sliding locking piston (30) back through the balls (34) until the balls are pushed out into the reservation of the Pinion tube (35) where the balls are maintain by the balls locking piston (33).

In this position, the sliding locking piston tip (31) maintains the front toothed pinion lock lever (29) down. This lever (29) controls the front toothed pinion locking (26) and so, the system is locked.

Figure 12:
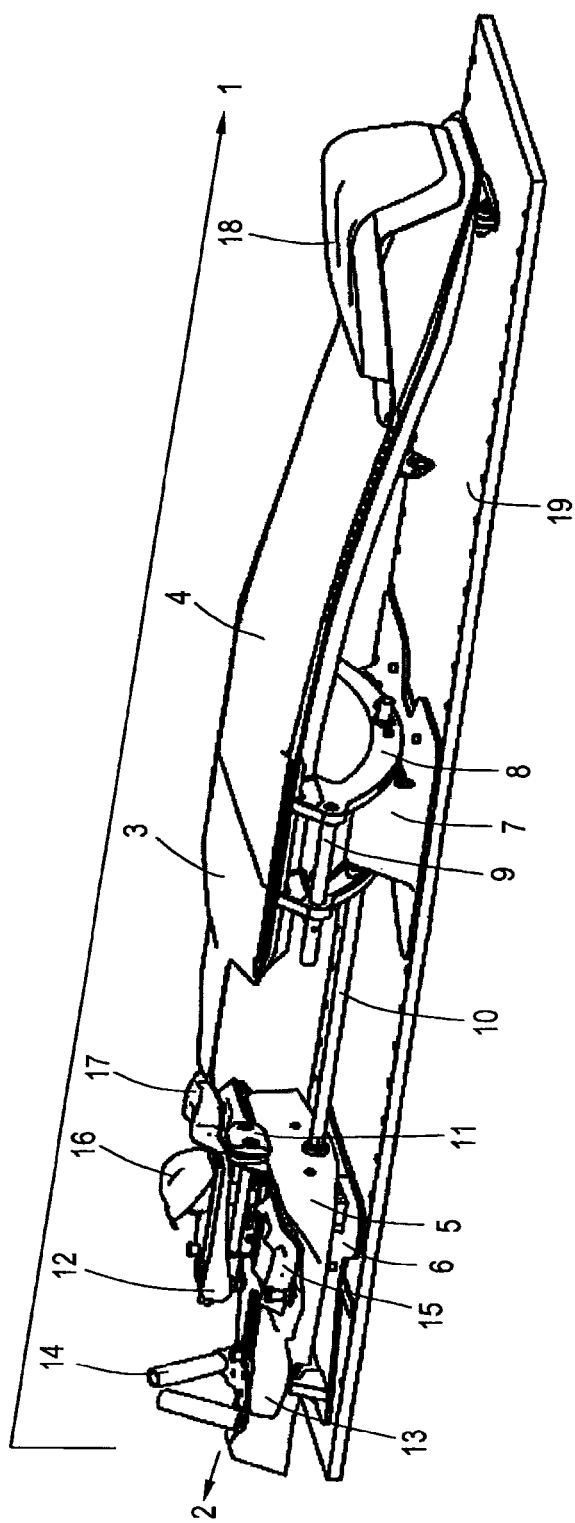

The assembled preferred device comprising cephalic, thoracic and caudal module and the preferred locking and synchronization mechanism is depicted in FIG. 12.

In the device according to the invention the portions of the modules that are adjacent to the irradiation source during treatment are preferably essentially radiolucent. The essentially radiolucent material may comprise a composite material, preferably carbon composite material. It more preferably does not comprise metallic parts in the portions of the modules that are adjacent to the irradiation source during treatment. The walls of at least the thoracic portion are preferably perforated to produce an open area.

The modules are preferably collapsible, to allow the device to be stowed away and/or transported in a collapsed way. The cephalic module, the thoracic module and the caudal module are adjustably connected by means that are suitable to fasten the three modules to each other. The connection is such that each module has a means for fastening the next module which is formed to receive a securing means for connecting the module to the next module.

The thoracic module preferably comprises holes, preferably symmetrical holes aligned on the side supporting the untreated breast. The triangular portion at the sternal interface is preferably adapted to the patient sternum anatomy. It is preferably padded with foam, which permits to decrease distortion of a CT planning beam.

The patient immobilization device of the present invention can preferably be attached to most standard patient tables or couches by various attachment means. The securing means can be a removable device or it is preferably integrated into the base structure with appropriately means, such as holes and pins, so that it universally fits most common patient tables.

The patient immobilization device of the present invention is adjustable in several ways. First, the device can be adjusted to fit most commercially available treatment tables. This adjustability provides complete flexibility in that the device of the present invention is self-contained and fits most existing procedure tables. There is no need for retro-fitting or additional clamping or securing means. The patient immobilization device of the present invention adjusts on two sides and can easily be centred on a procedure table because of its two-way adjustability. The device preferably is rapidly and easily assembled to form a rigid frame. The assembled device is then preferably clamped onto the scan or treatment table through standard perforations available on all commercial systems. In a preferred embodiment, two alignment bars are present, more preferably at the cephalic and thoracic module to ensure identical positioning in subsequent treatment. The system is preferably essentially composed from carbon fibre composites and thermosetting plastics, especially in the treatment area.

Applicants found that preferably the synchronising axis is removable once a selected inclination is set for the thoracic and the cephalic module. However, the synchronisation axis, if statically retained between the two modules, may lead to artefacts in both the image acquisition of a patient, as well as in the treatment, the latter potentially resulting in an increased risk for collateral damage due to undesired radiation exposure.

Furthermore, applicants found that if the axis is removed, and the modules disconnected, there is the potential for torsion between the two modules. While this may only result in a small deviation in the angle between the two modules, this may result in inaccuracies during the treatment, thereby reducing the effectiveness of the treatment while increasing risk for collateral radiation damage in a patient. Preferably therefore, the synchronisation element or axis is reversibly removable to reduce the artefact formation during patient imaging and/or treatment. More preferably, the co-rotation system further comprises a self-locking mechanism that immobilizes the co-rotation movement of the synchronised modules upon removal of the synchronisation element. Again more preferably, the rotationally immobilized modules are detachable after removal of the synchronisation element, to permit reproducibility of the patient position.

Accordingly, the present invention therefore also relates to a particularly preferred embodiment, wherein the synchronisation axis is removable after the inclination angle has been set to a certain value, and wherein the rotation mechanisms are locked automatically by the removal of the axis. Even more preferably, the actual removal of the axis should self-lock the rotational mechanism one or both modules, avoiding any deviation from the synchronised and set angle due to operator or patient moves.

A particularly preferred embodiment of the subject invention comprises a self-locking and quick release system in the co-rotation mechanism, which permits the operator to easily set the desired and identical angle for the synchronised modules, and subsequently allows removing the synchronisation axis, and to separate the modules, since the removal of the axis self-locks the co-rotational system, and hence fixes the inclination angle.

Accordingly, the present device preferably comprises a combined self-locking and fast release system, which when operably engaged, co-rotates the rotation mechanism of the two modules, while upon release self-locks these mechanisms such that there is no movement feasible, and allows the removal of the axis by an operator.

Figure 11A:
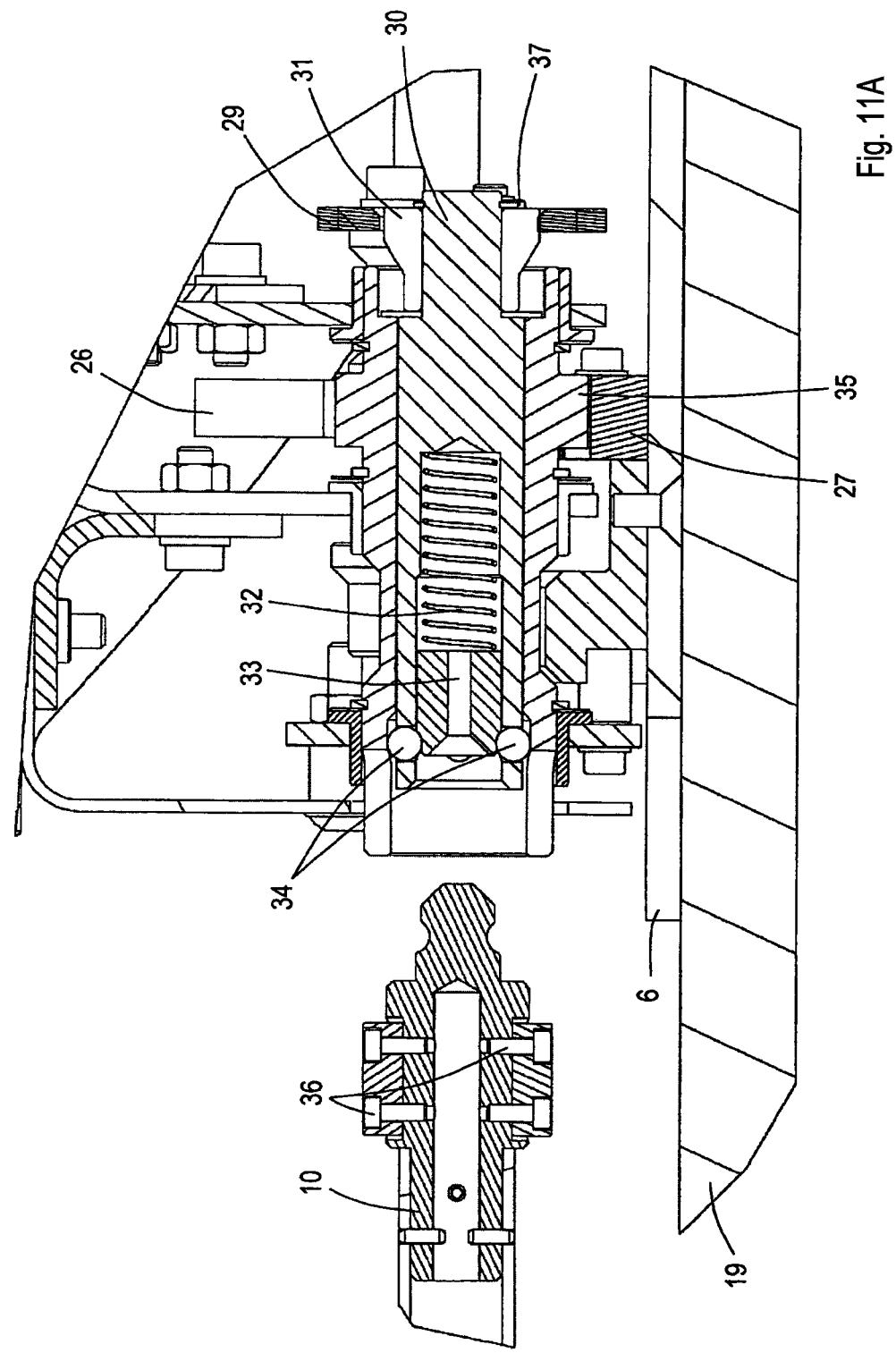
FIGS. 11a and b are cross-sectional depictions of a preferred connection of the synchronisation axis with the co-rotating and quick release mechanism, whereby
Figure 11B:
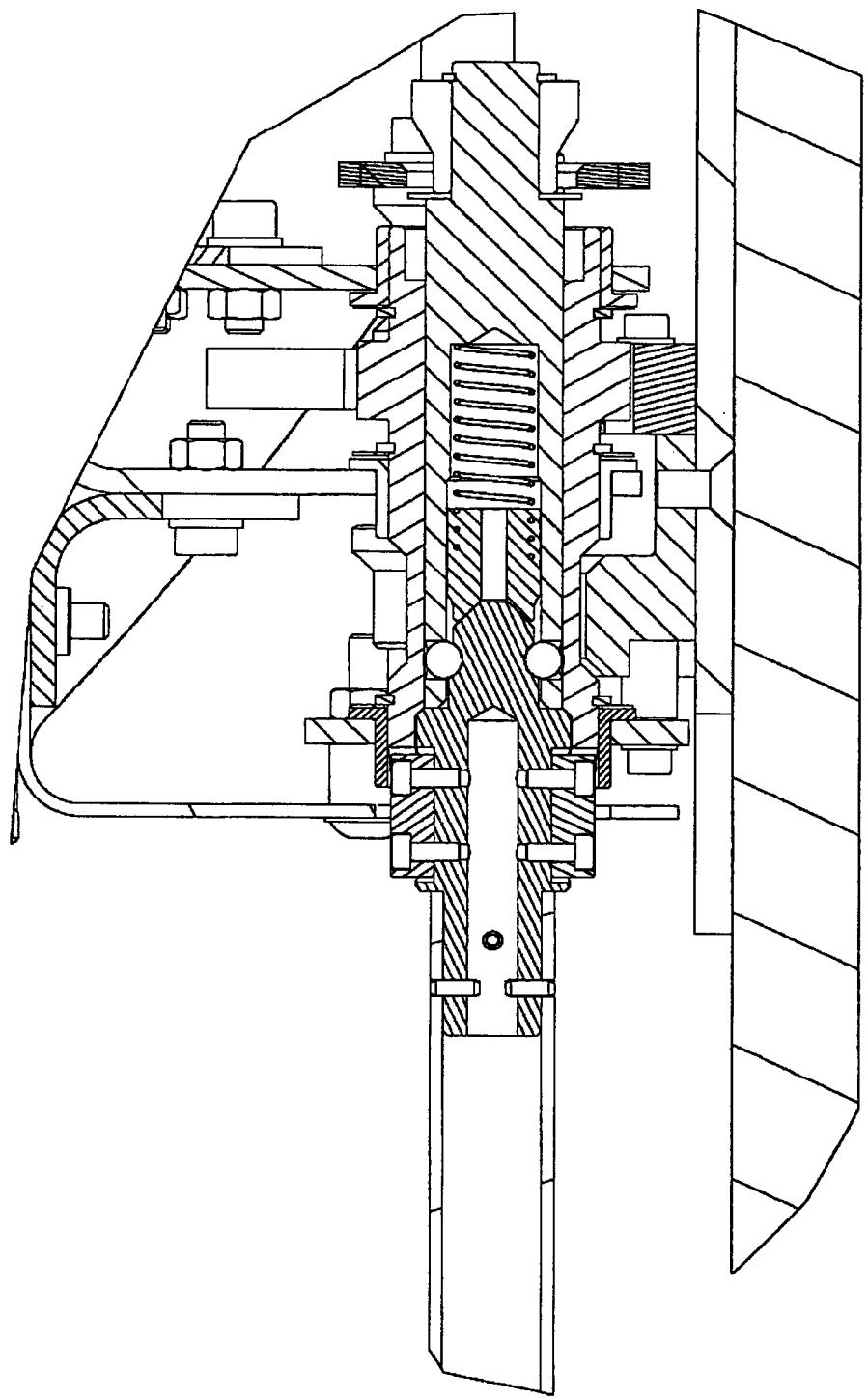

FIGS. 4a and 4b as well as FIGS. 11a and 11b show the operation of a particularly preferred embodiment of this system, which is characterised as follows: if the synchronisation axis is inserted, the system is unlocked for co-rotation.

There are indentations provided in the sliding locking piston (30), which contain the Socking balls (34). When the corotation synchronisation axis is removed, the sliding locking piston (30) is in the rear position. It cannot move further back because of the stop circlip (37); and it cannot move forward because at the same time, since the ball locking piston (33) maintains the locking balls (34) in the indentation of the Pinion tube (35). In this position, the sliding locking piston tip (31) maintains the front toothed pinion lock lever (29) down and engaged with front toothed pinion locking (26), thereby effectively locking the rotational system and prohibiting any pivotal rotational action.

When engaging the corotation shaft (30) into the sliding locking piston (30), the head of the shaft compress the spring (32) and pushes the balls locking piston (33) that unlock the balls.

The balls are going into the grove of the shaft head and so the sliding locking piston (30) can slide forward, pushed by the synchronisation axis shaft head through the balls.

In forward position, the shape of the sliding piston tip (31) allows to release the front toothed pinion lock lever. This lever may pulled up by a spring and thus activate the front toothed pinion lock (26) to the upper position, which thereby unlocks the rotational mechanism.

The co-rotation motion is transmitted from the rotation of the synchronisation axis by the corotation keys (36) that are inserted at the same time into fitting slots on the pinion tube (38).

Conversely, the co-rotation system locking works in reverse order: When removing the synchronisation axis, the shaft pulls the sliding locking piston (30) back through the balls (34) until the balls are pushed out into the reservation of the Pinion tube (35) where the balls are maintained by the balls locking piston (33).

In this position, the sliding locking piston tip (31) maintains the front toothed pinion lock lever (29) in the lower position, thereby locking the rotational movement. Since this lever (29) controls the front, toothed pinion lock (26), the system is locked.

Performance of the device is directly influenced by the material used for its construction. Lighter elements are preferred over heavier elements. For example, the lighter elements in composites and polymer materials result in less elastic and inelastic radiation scattering compared to materials containing metals or alloys. In addition, fluorescence is reduced. For example, when a metal atom is impacted by radiation, it absorbs the radiation energy by ejecting an electron from its shell in the atom's electron cloud. When an electron falls back into the shell, radiation is emitted. This effect is known as fluorescence. Because the radiation can be emitted in any direction, the patient can be subjected to an undirected dose of radiation energy.

Metals are also undesirable due to their high radiation absorption compared to plastics and carbon composite. Because of the high radiation absorption, the use of metals in the device can also reduce the therapy dose available to the patient.

All components of the present invention can be non-metallic although some metallic parts can be used if they do not disrupt the performance of the device. The individual components may be selected based on the intended use of the device, but advantageously are crafted from materials that are essentially radiolucent, such as carbon fibre epoxy resin composite. This particular feature is especially important if a highly oblique angle must be used for treating the patient where the device could come into the line of the high-energy beam.

A radiolucent device allows imaging and treatment of a patient through the patient immobilization device. This increases the treatment flexibility by allowing an accurate attack of the cancer or tumour from ail aspects and angles.

The present invention can be used in conjunction with most available tables as well as most available accessories that can be used with the patient immobilization device.

This description and the Figures illustrate examples of the present invention and are in no way meant to be limiting. Several different specific designs are contemplated by the inventors without parting from the original scope of the present, invention and would be easily recognizable by those skilled in the art. Whereas the invention has been shown and described in connection with the preferred embodiments thereof, it will be understood that many modifications, substitutions and additions can be made which are within the intended broad scope of the following claims.

The invention claimed is:

1. A patient immobilisation device for positioning a patient in the prone position for breast irradiation, comprising
   a cephalic module for supporting the head and upper extremities of the patient,
   a thoracic module for supporting the patient thorax, and shaped to allow at least one breast to extend below the thoracic module, and
   a caudal module for supporting the pelvis and lower extremities of the patient, wherein the cephalic module is detachable and securable to the thoracic module; and
   wherein the thoracic module is detachable and securable to the caudal module;
   characterised in that the device can be pivoted in an indexed way around a craniocaudal patient axis F.

2. The device according to claim 1, further comprising a co-rotation system for controlling of the pivoting motion of at least the cephalic and thoracic module.

3. The device according to claim 2, wherein the co rotation system comprises
   a) at least a primary lock and at least a secondary lock, and
   b) at least a synchronizing element that controls and coordinates a movement of the primary and the secondary lock.

4. The device according to claim 3, wherein the primary lock has a human interface allowing an operator to change inclination of the patient manually.

5. The device according to claim 3, wherein the secondary lock is moved by the movement of the primary lock through the synchronizing axis.

6. The device according to claim 3, wherein the caudal and the cephalic modules may be adjusted separately prior to locking and co-rotating the primary and the secondary lock with the synchronizing element, and moved by the movement of the primary lock.

7. The device according to claim 2, wherein a synchronisation element or axis is reversibly removable to reduce artefact formation during patient imaging and/or treatment.

8. The device according to claim 7, wherein the co-rotation system further comprises a self-locking mechanism that immobilizes a co-rotation movement of the synchronised modules upon removal of the synchronisation element.

9. The device according to claim 8, comprising: a sliding locking piston, locking balls, a stop circlip; a bail locking piston, and a pinion tube; whereby the sliding locking piston and the locking balls are operably placed such that if a corotation synchronisation axis is removed; the sliding locking piston is maintained immovable in a rear position by a stop circlip; and a ball locking piston maintaining the locking bails in indentation of a pinion tube; whereby the sliding locking piston tip maintains a front toothed pinion lock lever in a lower position and engaged with front toothed pinion locking, thereby effectively locking the co-rotational system and prohibiting any pivotal rotational action.

10. The device according to claim 9, further comprising a spring whereby when engaging the synchronisation axis corotation shaft into the sliding locking piston, the head of the shaft compress the spring and pushes the balls locking piston that unlock the bails to go into a grove of the shaft head permitting the sliding locking piston to slide forward pushed by the corotation shaft head through the bails, thereby releasing the front toothed pinion lock lever into an upper position, and thus unlocking the rotational mechanism, while permitting co-rotation motion to be transmitted from the rotation of the synchronisation axis though the corotation keys inserting into fitting slots on the pinion tube.

11. The device according to claim 7, wherein rotationally immobilised modules are detachable after removal of the synchronisation element without, affecting settings of the co-rotation mechanism in order to not disturb alignment when reassembling the modules, to permit reproducibility of the patient position.

12. The device according to claim 1, wherein portions of the modules that are adjacent to an irradiation source during treatment are essentially radiolucent.

13. The device according to claim 12, wherein the portions of the modules that are adjacent to a the irradiation source during treatment comprise a composite material.

14. The device according to claim 1, wherein the device is adaptable to be reproducibly secured to a treatment table.

15. The device according to claim 1 for providing a comfortable and ergonomic position for the patient during treatment, wherein the modules are secured adaptably and indexed to each other to fit the patient anatomy.

16. The device according to claim 1, further comprising a mechanical support structure guiding a position of at least the cephalic and thoracic module.

17. The device according to claim 1, wherein the device can be pivoted in an indexed way around a craniocaudal patient axis F at an angle of from −10° to +10°.

18. The device according to claim 1, wherein the modules are collapsible, to allow the device to be stowed away and/or transported in a collapsed way.

19. The device according to claim 1, wherein walls of at least the thoracic portion are perforated to produce an open area.

20. A process for the scanning and/or selective breast irradiation of a patient, comprising
providing a cephalic module for supporting the head and upper extremities of the patient, a thoracic module for supporting the patient thorax, and shaped to allow at least one breast to extend below the thoracic module, and a caudal module for supporting the pelvis and lower extremities of the patient, wherein the device can be pivoted in an indexed way around a craniocaudal patient axis F, and wherein the cephalic module is detachable and securable to the thoracic module; and wherein the thoracic module is detachable and securable to the caudal module; and subjecting at least a portion of the breast extending below the thoracic module to an ionization radiation for a suitable period of time and at a suitable radiation rate.

21. A process for scanning or selective breast irradiation of a patient, comprising the steps of
positioning the patient by using the device according to claim 1; and
conducting scanning or selective breast irradiation.

* * * * *